United States Patent
Medding

(10) Patent No.: US 7,080,771 B2
(45) Date of Patent: Jul. 25, 2006

(54) METHOD FOR CHECKING THE QUALITY OF A WEDGE BOND

(75) Inventor: Jonathan Medding, Birmensdorf (CH)

(73) Assignee: ESEC Trading SA, Cham (CH)

( * ) Notice: Subject to any disclaimer, the term of this patent is extended or adjusted under 35 U.S.C. 154(b) by 25 days.

(21) Appl. No.: 10/863,303

(22) Filed: Jun. 8, 2004

(65) Prior Publication Data
US 2004/0256438 A1   Dec. 23, 2004

(30) Foreign Application Priority Data
Jun. 18, 2003   (CH) ..................... 1087/03

(51) Int. Cl.
*B23K 31/12*   (2006.01)
*B23K 20/00*   (2006.01)
(52) U.S. Cl. ............... 228/103; 228/102; 228/180.5
(58) Field of Classification Search .............. None
See application file for complete search history.

(56) References Cited

U.S. PATENT DOCUMENTS

| 4,040,885 A | * | 8/1977 | Hight et al. ............... 156/378 |
|---|---|---|---|
| 5,591,920 A | | 1/1997 | Price et al. |
| 5,894,981 A | | 4/1999 | Kelly |
| 2004/0079790 A1 | * | 4/2004 | Mayer et al. ............ 228/180.5 |
| 2004/0226983 A1 | * | 11/2004 | Walther ..................... 228/56.5 |

* cited by examiner

*Primary Examiner*—Lynne R. Edmondson
(74) *Attorney, Agent, or Firm*—McCormick, Paulding & Huber LLP

(57) ABSTRACT

A method for checking the quality of a wedge bond between a wire loop and a connection point on a substrate, whereby the wire loop was formed by means of a capillary of a Wire Bonder, is characterised by the following steps:
  Placing the capillary at a side of the wire loop and next to the wedge bond, whereby the tip of the capillary is located below the level of the wire loop.
  Moving the capillary parallel to the surface of the substrate and orthogonally to the wire loop until the wedge bond tears away from the connection point or the wire breaks, and simultaneously measuring a signal that is a measure for a force exerted by the capillary on the wire loop, and
  Determining the maximum of the measured signal.

2 Claims, 1 Drawing Sheet

METHOD FOR CHECKING THE QUALITY OF A WEDGE BOND

PRIORITY CLAIM

Figure 1:
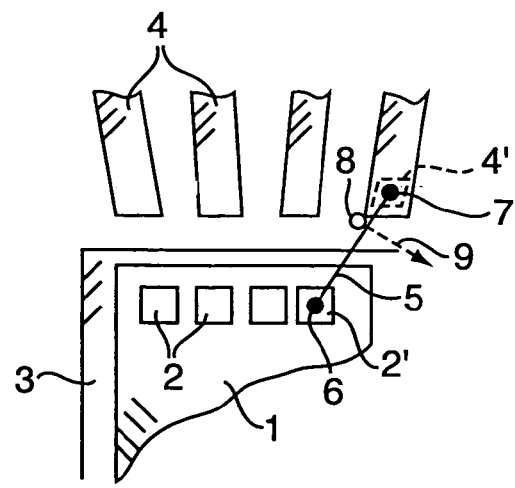

The present application claims priority under 35 U.S.C § 119 based upon Swiss Patent Application No. 2003 1087/03 filed on Jun. 18, 2003, the disclosure of which is herein incorporated by reference.

FIELD OF THE INVENTION

The invention concerns a method for checking the quality of a wedge bond.

BACKGROUND OF THE INVENTION

A Wire Bonder is a machine with which wire connections are made to semiconductor chips after they have been mounted on a substrate. The Wire Bonder has a capillary that is clamped to the tip of a horn. The capillary serves to secure the wire to a connection point on the semiconductor chip and to a connection point on the substrate as well as to guide the wire between the two connection points. On making the wire connection between the connection point on the semiconductor chip and the connection point on the substrate, the end of the wire protruding from the capillary is first melted into a ball. Afterwards, the wire ball is secured to the connection point on the semiconductor chip by means of pressure and ultrasonics. In doing so, ultrasound is applied to the horn from an ultrasonic transducer. This process is known as ball bonding. The wire is then pulled through to the required length, formed into a wire loop and welded to the connection point on the substrate. This last process is known as wedge bonding. After securing the wire to the connection point on the substrate, the wire is torn off and the next bond cycle can begin.

Ball bonding as well as wedge bonding are influenced by various factors. In order to achieve bond connections of a predetermined quality, the adequate values of several physical and/or technical parameters must be determined for a particular process. Examples of such parameters are:

the bond force, that is the normal force which the capillary exerts on the ball bond or the connection point of the semiconductor chip during the bonding process, a parameter, designated herein as ultrasonic variable P, which controls the application of ultrasound to the ultrasonic transducer. The ultrasonic variable is, for example, the amplitude of the alternating current which flows through the ultrasonic transducer of the horn or the amplitude of the alternating voltage which is applied to the ultrasonic transducer, or the power, or another variable, a time duration, designated herein as ultrasonic time T, which indicates the length of time that the ultrasonic variable P is applied to the ultrasonic transducer, the impact velocity of the capillary on the connection point, a binary parameter that indicates whether the ultrasonic variable is already applied to the ultrasonic transducer before the capillary impacts on the connection point.

Today, in order to characterise the bond quality in the sense of a quality control as well as to determine the optimum bond parameters, two methods are primarily used namely a) a so-called Pull Test, with which the force is measured at which the bond tears away from the semiconductor chip or substrate when the bond is pulled in, vertical direction in relation to the surface of the semiconductor chip or substrate, and b) a so-called Shear Test, with which the force is measured at which the bond tears away from the semiconductor chip or substrate when the bond is pushed away parallel to the surface of the semiconductor chip or substrate by means of a tool.

These tests are normally carried out with equipment specially developed for this application. However, from the patent U.S. Pat. No. 5,894,981, a Wire Bonder is known which is set up to carry out a Pull Test. This Wire Bonder concerns a specific method for forming the wire loops with which the wire is not fed by a capillary. With the Pull Test, after forming the wedge bond, the wire is pulled away in a direction running vertically to the surface. The disadvantage with this test is that the check takes place before the bond cycle is completed as the wedge bond is still connected to the wire feed device.

From the patent U.S. Pat. No. 5,591,920, a Wire Bonder is known which is set up to carry out a Pull Test with which the maximum current is measured which flows through a motor that raises and lowers the capillary. This test can be carried out for Ball Bonds as well as for Wedge Bonds. When this Pull Test is carried out for a Wedge Bond, then an important disadvantage exists in that, on testing, load is not put on the wedge as with the established Pull Test, but on the piece of wire which is to be torn off in the last stage of the bond cycle, the so-called tail.

SUMMARY OF THE INVENTION

The object of the invention is to develop a more suitable test for checking the quality of a wedge bond.

In accordance with the invention, the checking of the quality of a wedge bond takes place in that the capillary of the wire bonder is used to push the wire loop formed between a first connection point on a semiconductor chip and a second connection point on a substrate, away at right angles to the longitudinal direction of the wire loop, until the wedge bond takes off or the wire breaks, whereby the capillary is applied close to the second connection point.

The test takes place with a method that is characterized by the following steps:

Placing the capillary at a side of the wire loop and next to the wedge bond, whereby the tip of the capillary is located below the level of the wire loop.

Moving the capillary parallel to the surface of the substrate and orthogonally to the wire loop until the wedge bond tears away from the connection point or the wire breaks, and simultaneously measuring a signal that is a measure for a force exerted by the capillary on the wire loop, and Determining the maximum of the measured signal.

DETAILED DESCRIPTION OF THE PREFERRED EMBODIMENTS

The test can be performed immediately after the production of the wire loop. The single steps are now explained in detail:

1. With a normal bond cycle, a wire loop is formed between a first connection point on the semiconductor chip and a second connection point on the substrate. The bond connection on the first connection point usually is a so-called "ball" bond, the bond connection on the second connection point is a so-called "wedge"

bond. After forming the wedge bond, the wire is torn off as usual and a new wire ball is formed on the capillary.

2. The capillary of the Wire Bonder is placed at one side of the formed wire loop without touching the wire loop. The tip of the capillary is located below the level of the wire loop.

3. The capillary is moved parallel to the surface of the substrate and orthogonally, i.e. at right angles, to the wire loop. In doing so, it comes into contact with the wire, pulls and stretches the wire until finally the wedge bond tears away or the wire breaks. During this movement, the signal of a sensor that is a measure for the force exerted by the capillary on the wire loop is measured continually and afterwards the maximum of this signal is determined. This maximum is a measure for the force that was necessary in order to tear off the wire.

The sensor is for example a force sensor integrated into the bondhead. The force sensor measures the force exerted by the horn at the tip of which the capillary is clamped on the bondhead.

The bondhead has two drives which enable the movement of the capillary parallel to the surface of the substrate. One of the two drives can serve as the sensor, whereby the sensor signal is the current flowing through the drive. The movement of the capillary must run orthogonally to the longitudinal direction of the wire loop. It is of advantage to align the longitudinal direction of the wire loop relative to the axis of movement of the bondhead such that only one of the two drives is necessary for moving the capillary orthogonally to the longitudinal direction of the wire loop. In this case only the current flowing through this drive has to be measured and analyzed.

If the longitudinal direction of the wire loop with respect to the movement axis of the bondhead is not aligned specially and if therefore both drives are necessary in order to move the capillary orthogonally to the longitudinal direction of the wire loop then either the current flowing through one of the two drives can be used as sensor signal or the currents flowing through the two drives can be measured and a single sensor signal formed from them.

BRIEF DESCRIPTION OF THE DRAWING FIGURES

The accompanying drawings, which are incorporated into and constitute a part of this specification, illustrate the placing of the capillary in step 2 and its movement in step 3. The figures are not to scale.

Figure 2:
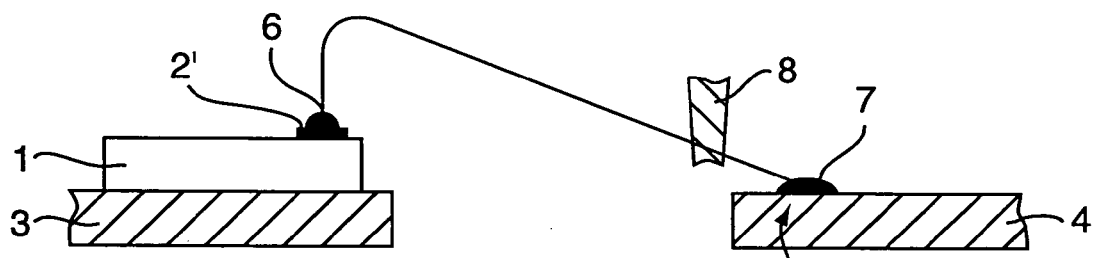
Figure 3:
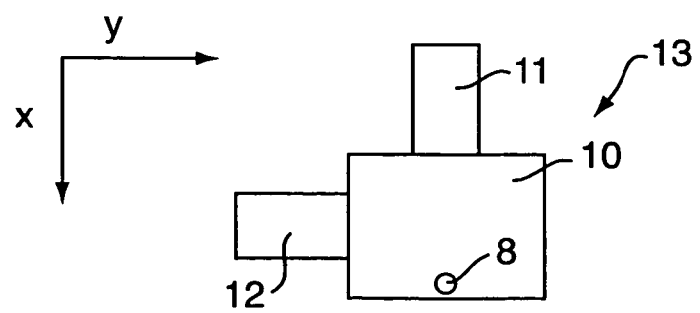

In the drawings:

FIGS. 1 and 2 show a plan and side view of a wire loop and a capillary of a wire bonder that formed the wire loop and is used in accordance with the invention in order to check the quality of the wire loop, and FIG. 3 shows a plan view and schematically the bondhead of the Wire Bonder and two drives for the movement of the bondhead in the horizontal plane.

FIG. 1 shows schematically a plan view of a semiconductor chip 1 with several connection points 2 and a substrate 3 with several connection fingers 4. A wire loop 5 is formed between a first connection point 2' on the semiconductor chip 1 and a second connection point 4' on one of the connection fingers 4. The wire loop 5 is attached to the connection point 2' with a ball bond 6 and to the connection point 4' with a wedge bond 7. The wire loop 5 was formed by means of a capillary 8 that is mounted on a not presented bondhead of a Wire Bonder. The capillary 8 is located to the side of the wire loop 5 at a height at which its tip is below the level of the application point of the capillary 8 on the wire loop 5. This condition is shown in FIG. 2, it corresponds to the condition after carrying out step 2 of the process explained above. FIG. 2 also shows the direction of movement 9 of the capillary 8 during step 3 of the process explained above.

With this test, the quality of the wedge bond should be determined. For this reason, in process step 2 the capillary 8 is placed next to the wedge bond 7 so that the force exerted by the capillary 8 on the wire loop 5 is transmitted from the wire to the wedge bond 7 so that the wedge bond 7 between the wire and the connection finger 4' tears away and the wire itself is not torn in two.

FIG. 3 shows in plan view and schematically the bondhead 10 of the Wire Bonder and two drives 11 and 12 for the movement of the bondhead in the plane 13. In this example the two drives 11 and 12 are linear motors with movement axes x and y running orthogonally to each other, whereby the linear motors allow also a movement of the bondhead orthogonally to their respective movement axis. The linear motors each consist of a stator and a coil connected to the bondhead. Such a bondhead is known for example from U.S. Pat. No. 5,114,302. The direction of the wire loop 5 (FIG. 1) is advantageously chosen such that the direction of movement 9 of the capillary 8 runs either parallel to the x-axis or parallel to the y-axis. If the direction of movement 9 of the capillary 8 runs parallel to the x-axis then the current flowing through the drive 11, i.e. with this example the current flowing through the coil, can be used as the sensor signal. The invention can also be implemented on any other Wire Bonder, for example on a Wire Bonder with a rotative bondhead according to U.S. Pat. No. 6,460,751.

The invention has been described by means of a widely known standard process with which the connection on the first connection point is a so-called ball-bond and the connection on the second connection point is a so-called wedge-bond. As it is aimed to determine the quality of the wedge bond on the second connection point the bond connection on the first connection point can be any arbitrary bond connection, for example also a wedge-bond. But in this case the invention can be used to either testing the quality of the wedge-bond on the first connection point or the quality of the wedge-bond on the second connection point. In the first case the capillary 8 has to be placed next to the first connection point and in the second case as described by means of the sample above next to the second connection point laterally besides the wire loop 5.

The substrate is given by the application. The substrate is for example a leadframe or a tape or foil with printed circuits or even a semiconductor chip if semiconductor chips are mounted directly on above each other (so-called stagged-die application).

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims and their equivalents.

What is claimed is:

1. A method for checking the quality of a wedge bond formed between a wire loop and a connection point on a substrate, wherein the wire loop has been formed by means of a capillary of a wirebonder, the method comprising the following steps:

placing the capillary of the wire bonder at a side of the wire loop and next to the wedge bond, wherein a tip of the capillary is located below a level of the wire loop, moving the capillary parallel to a surface of the substrate and orthogonally to the wire loop until the wedge bond tears away from the connection point or the wire breaks, and simultaneously measuring a signal that is a measure for a force exerted by the capillary on the wire loop, and
determining a maximum of the measured signal.

2. The method according to claim 1, wherein the signal is a strength of a current that flows through a drive moving the capillary.

* * * * *